United States Patent [19]

Poler

[11] 4,434,515
[45] Mar. 6, 1984

[54] INTRAOCULAR LENS
[75] Inventor: Stanley Poler, New York, N.Y.
[73] Assignee: Lynell Medical Technology Inc., New York, N.Y.
[21] Appl. No.: 402,037
[22] Filed: Jul. 26, 1982
[51] Int. Cl.³ .......................... A61F 1/16; A61F 1/24
[52] U.S. Cl. ......................................................... 3/13
[58] Field of Search ........................................ 3/13, 1

[56] References Cited

U.S. PATENT DOCUMENTS

| | | | |
|---|---|---|---|
| 4,122,556 | 10/1978 | Poler | 3/13 |
| 4,134,160 | 1/1979 | Bayers | 3/13 |
| 4,249,271 | 2/1981 | Poler | 3/13 |
| 4,280,232 | 7/1981 | Hummel | 3/13 |
| 4,298,994 | 11/1981 | Clayman | 3/13 |
| 4,316,293 | 2/1982 | Bayers | 3/13 |
| 4,343,050 | 8/1982 | Kelman | 3/13 |

Primary Examiner—Ronald L. Frinks
Attorney, Agent, or Firm—Hopgood, Calimafde, Kalil, Blaustein & Judlowe

[57] ABSTRACT

The invention contemplates haptic construction for support of a finished intraocular lens element, wherein the haptic has plural radially outward stabilizing-leg formations, which incorporate a feature of radial adaptability in terms of the anterior-chamber wall size to which the lens may be fitted. Various embodiments are described to illustrate application to a single-piece and to multiple-piece haptics, and to illustrate radially compliant yieldability as well as ratchet-retention of a selected radial span of the stabilizing leg formations.

24 Claims, 13 Drawing Figures

INTRAOCULAR LENS

BACKGROUND OF THE INVENTION

This invention relates to structures for making an improved lens implant, as a replacement for a cataract-clouded or otherwise diseased natural lens. The invention represents improvement over structures described in my U.S. Pat. Nos. 4,122,556 and 4,249,271 and over my various other patent disclosures referred to therein. Reference is therefore made to said patents and disclosures for greater background detail as to structure, and as to manufacturing and manipulating technique.

The invention is particularly directed to structure which relies upon the wall of an eye chamber, for example the wall of the anterior chamber, to derive centrally stabilized positioning support for the implanted lens element. But the chamber-wall size will vary from one patient to another. In the past, it has been necessary to measure and prescribe adapter mount (haptic) structure of size suited to the patient's eye-chamber dimensions, and this requirement dictates the need for an inventory of different haptic sizes, as well as the need to make accurate wall measurement prior to surgical implantation.

BRIEF STATEMENT OF THE INVENTION

It is an object of the invention to provide improved mounting or haptic structure for an intraocular lens.

It is a specific object of the invention to provide inherent adaptability to differences in chamber-wall size, in mounting structure of the character indicated.

Another specific object is to meet the above objects with structure having gently compliant self-adaptability to wall size.

A further specific object is to provide such structure wherein radial extent of stabilizing support can be preselected and retained.

A still further object is to meet the above objects for the cases of single-piece and multiple-piece haptics.

In connection with all the foregoing objects, it is an object to provide inherently secure and accurate intraocular positioning of an optically finished glass lens element.

The foregoing and other objects and features of the invention are achieved in an illustrative series of embodiments wherein annular haptic structure axially retains itself against both axial sides of the peripheral rim of the lens element to which it is assembled. The haptic body has plural radially outward stabilizing feet and is formed from compliant sheet material. Angularly adjacent feet are adjustably interconnected in such manner as to enable corresponding adjustment of the radial limit of stabilizing support which they provide. In some forms, the adjustment is compliantly self-adapting, from a larger radius to such lesser radius as the particular eye-chamber wall may dictate. In other forms, the particular radius may be preselected or preset, by means of an adjusted ratchet-engaged relation.

DETAILED DESCRIPTION OF PREFERRED EMBODIMENTS

An illustrative variety of preferred embodiments will be described in conjunction with the accompanying drawings. In said drawings.

Figure 1:
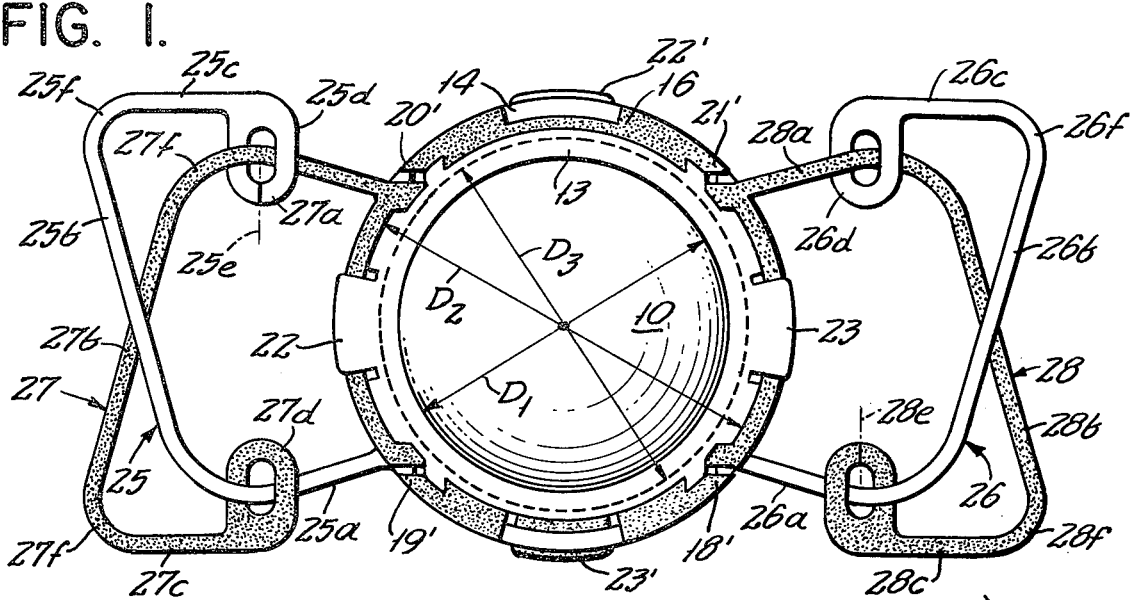
FIG. 1 is a view in elevation of an intraocular lens of the invention, complete with assembled haptic structure, in readiness for self-adapting surgical implantation.
Figure 2:
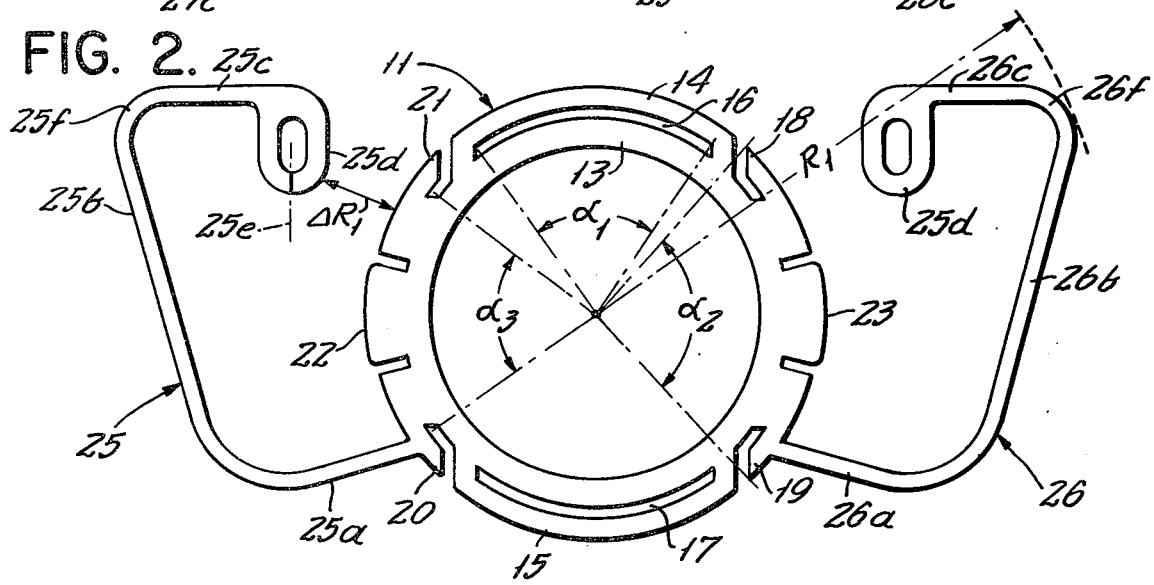
FIGS. 2 and 3 are blank outlines of the respective parts of the haptic of the intraocular lens of FIG. 1.
Figure 3:
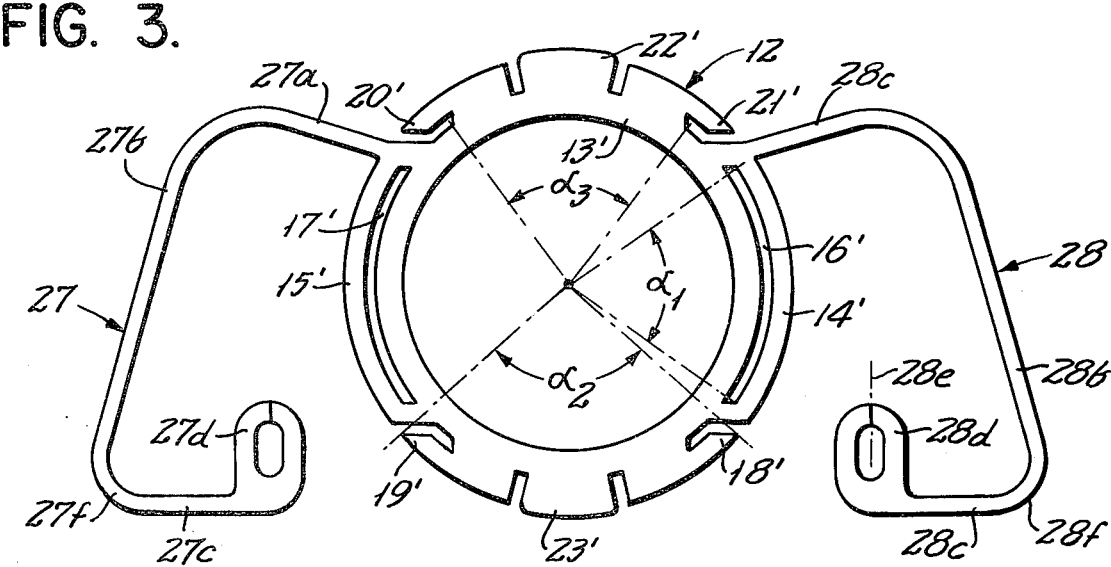

In FIGS. 1 to 3, the invention is shown in application to mounting (haptic) structure for a finished optical lens element 10 to be surgically implanted in a human eye, relying upon chamber-wall contact, for example, the wall of the anterior chamber, for stabilized support of the implant, as at the scleral ridge. The haptic structure comprises two parts 11 (FIG. 2) and 12 (FIG. 3) of thin-sheet compliant flexible material, and these parts circumferentially continuously overlap opposite axial sides of the rim or peripheral region of lens 10 and are connected to each other at angularly spaced locations adjacent the lens periphery. Each of these parts 11(12) is characterized by a circumferentially continuous annular body portion 13(13') having a circular inner edge of diameter $D_1$ less than the diameter $D_2$ of lens 10 and otherwise in full radial overlap with the lens periphery; because of similarity of certain features of parts 11 and 12, the same identifying numbers for features of part 11 (FIG. 2) are adopted for corresponding features of part 12 (FIG. 3), with primed notation. Thus, with the parts 11-12 assembled to each other and to lens element 10 in FIG. 1, and assuming part 11 to be ultimately the posterior part, the body portion 13 of part 11 circumferentially continuously laps the posterior side of the peripheral region of the lens element, and the body portion 13' of anterior part 12 similarly laps the corresponding anterior region of the lens element.

For connected assembly of parts 11-12 to each other, the peripheral regions of both body portions 13-13' are similarly formed with hook and slot formations having diametrically opposite symmetry in diametrically opposite quadrants about the central axis. Thus, within a first pair of diametrically opposed quadrants, first and second diametrically symmetrical extensive arcuate tab projections 14-15 are formed with arcuate slots 16-17, of substantial angular extent $\alpha_1$ approaching but less than 90 degrees. And within the second pair of diametrically opposed quadrants, first and second pairs of diametrically symmetrical hook formations 18-19 and 20-21 project in the circumferentially outward direction with respect to the involved quadrant. The hook formations of member 11 are designed for interlocked engagement in the arcuate-slot formations 16'-17' of the other member 12, while the hook formations 18'-19' and 20'-21' of member 12 have interlocked engagement in the arcuate-slot formations of member 11. To this end, the hook ends in a given quadrant are at an angular spread $\alpha_2$ which exceeds the effective slot width $\alpha_1$, and the closed ends of the hook openings in a given quadrant are at an angular spread $\alpha_3$ which is less than the effective slot width $\alpha_1$. Finally, radial tabs 22-23 at diametrically opposed locations (between hooks 20-21 and 18-19, respectively) enable reinforcing back-up of the arcuate tabs 15'-14' between limits of associated hook engagements to slots 17'-16', as will be clear from inspection of FIG. 1.

In accordance with a feature of the invention, the annular body of the haptic is characterized by radially outward feet 25-26-27-28 at angularly spaced locations. These feet also extend toward and engage each other in pairs, the feet of each pair being cooperatively and compliantly yieldable to define a self-adapting outer radial limit of stabilizing support contact within the eye, the adaptation being to the particular radial limitations of the patient's eye chamber. As shown, two of these feet (25-26) are integral formations of haptic element 11, and the other two are integral formations of element 12. The foot 25 comprises a root portion 25a which extends generally radially outward, and an angularly extensive intermediate portion 25b extends generally at a right angle to root portion 25a; finally, a generally radially inward end portion 25c depends integrally from the outer end of portion 25b, to a point of inward termination at a loop formation 25d. All other feet 26-27-28 are similarly formed and have therefore been given similar qualifying symbols, as appropriate, it being noted that the intermediate portions 25b-27b (26b-28b) of adjacent pairs of feet extend in opposite directions over essentially the same angular span. The loop formation 25d is locally cut to permit assembly of the end of foot 25 to the root portion 27a of foot 27, the cut being designated at alignment 25e, and a similar cut of loop formation 27d enables similar assembly of the end of foot 27 to the root portion 25a of foot 24; correspondingly engaged relations exist for loop formation 26d to root portion 28a and for loop formation 28d to root portion 26a.

It will be noted that, for the described structure, the legs 25-27 (26-28) of each of the opposed pairs are engaged for their unstressed relation, to establish at 26f a maximum radius $R_1$ of stabilizing-support contact with an eye-chamber wall, and that for a smaller eye-chamber wall configuration the wall-contact point at bend 26f will be subjected to compliant radially inward displacement. In the course of such displacement the outer ends (25d . . . 28d) of all feet are guided along engaged root portions, a limiting inward displacement being reached when the outer ends (25d . . . 28d) contact the haptic body annulus. The radially inward spread $\Delta R_1$ for which radial adaptability exists is preferably at least one millimeter, thus enabling a FIG. 1 haptic of 13-mm maximum diametrical span ($2R_1$) to be self-adapting for wall limitations as small as 11-mm diameter.

Figure 4:
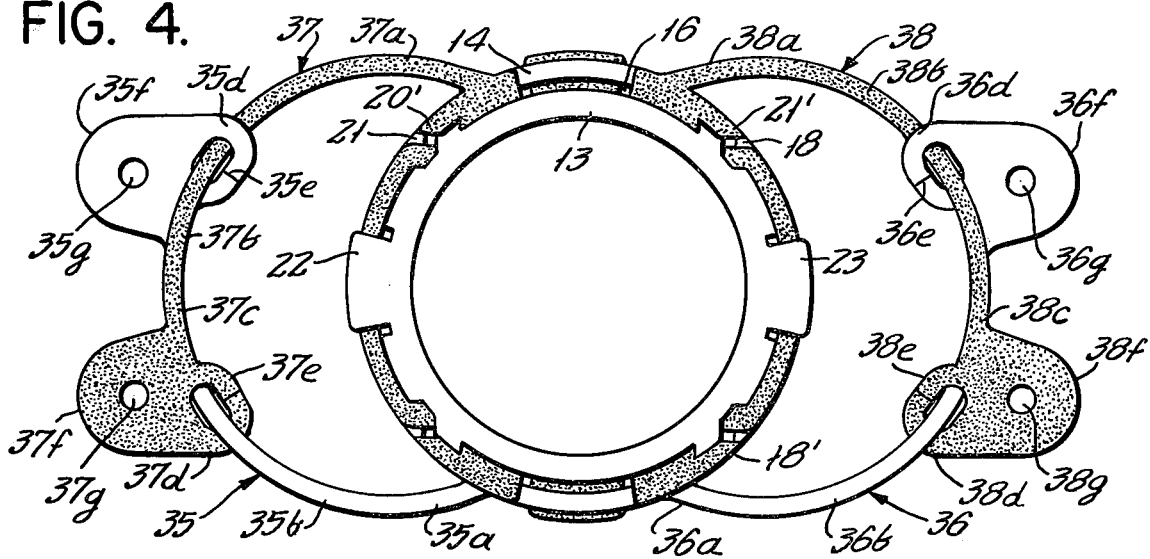
FIG. 4 is a view similar to FIG. 1, to show another embodiment.
Figure 5:
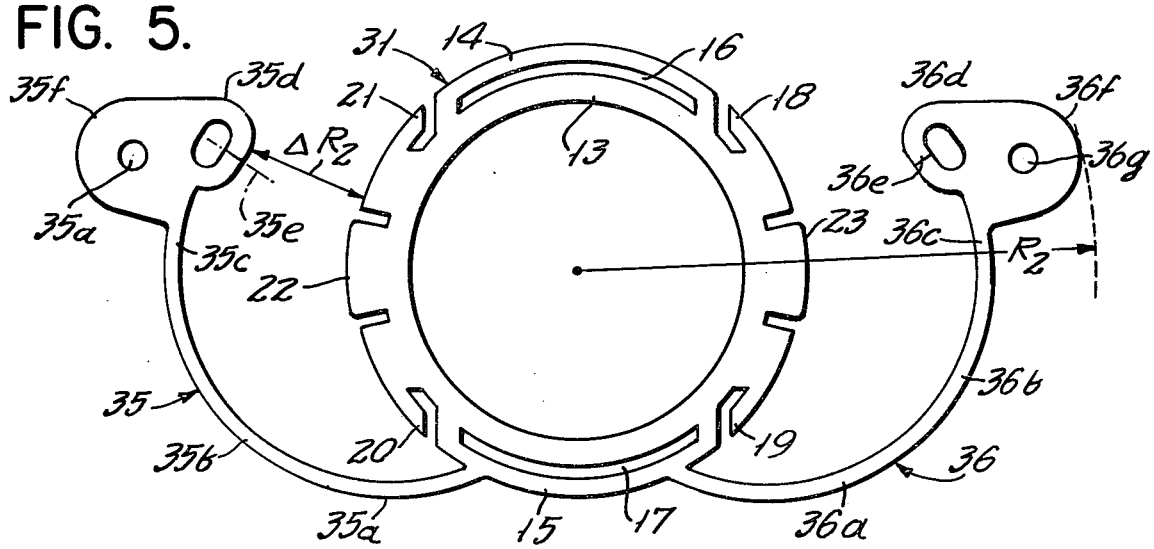
FIGS. 5 and 6 are views similar to FIGS. 2 and 3 to show haptic parts of FIG. 4.
Figure 6:
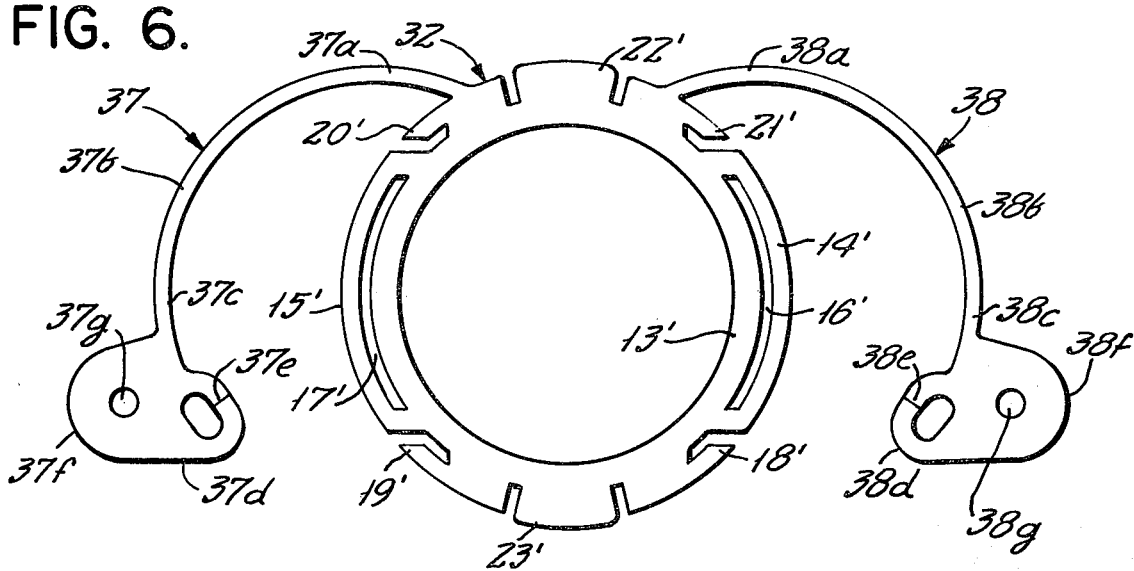

In the embodiment of FIGS. 4, 5 and 6, a haptic comprising two assembled parts is again employed. These parts 31 (FIG. 5) and 32 (FIG. 6) have engaged annular bodies meeting the description for FIGS. 2 and 3, and therefore the same reference numbers are used, as applicable. The difference in FIGS. 4, 5 and 6 is that the foot elements 35-36-37-38 are virtually continuously arcuate, e.g., in the case of foot 35, the generally radially outward root portion 35a merges continuously into the generally angularly extending intermediate portion 35b, which in turn merges continuously into the generally radially inward end portion 35c which includes a loop formation 35d. The loop formations of the adjacent feet of each pair (35-37, 36-38) have generally radially inward guided engagement with root portions, as previously described. For gently yieldable support via the described feet 35-36-37-38, each of them includes a radially outward lobe (35f . . . 38f) at maximum offset from the associated root-portion connection to the body annulus 13. In unstressed condition, the outer contour of lobes 35f . . . 38f establishes a maximum radius $R_2$ of chamber-wall stabilizing contact, and a slightly greater inwardly deflectable range $\Delta R_2$ (for example, 1.5 mm, for a 3-mm reduced diameter) is available for self-adaptation to particular eye-chamber sizes.

Figure 7:
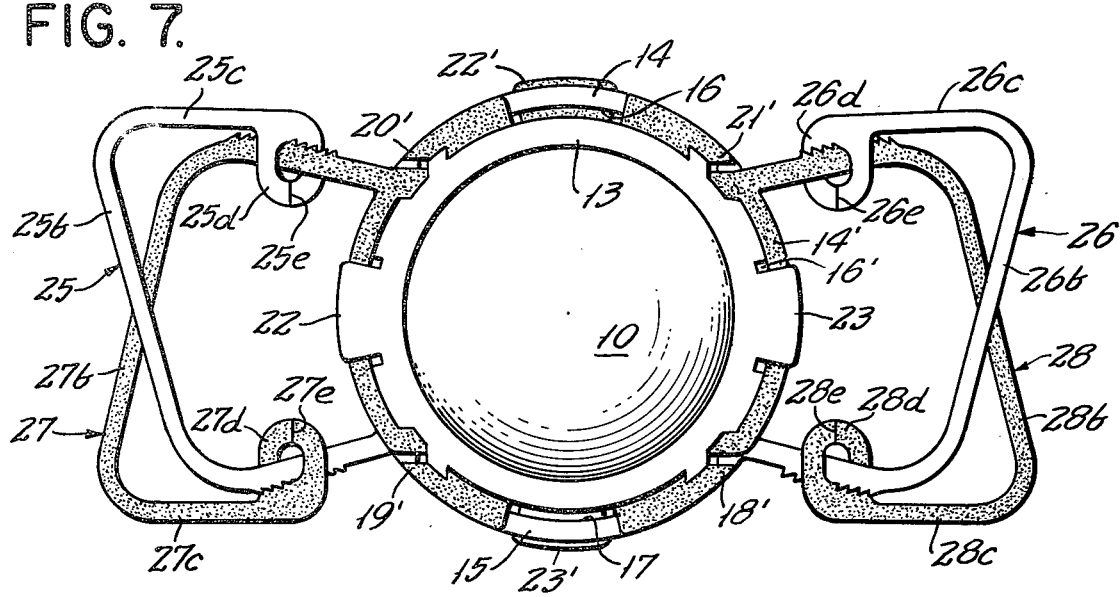
FIGS. 7 and 8 are views similar to FIG. 1 to show two further embodiments.

In the embodiment of FIG. 7, the parts may be as described for FIGS. 1 to 3, except that the edge profile of root portions 25a . . . 28a is of serrated nature, thus enabling the surgeon to achieve a ratchet-like retention of such reduction from the maximum radial span $R_1$ as he may deem appropriate for a particular patient's implantation. Having achieved a ratchet hold of the adjusted radial dimension, there is no residual preloading force of the haptic on the chamber wall, beyond that attributable to the negligible gravitational weight of the lens and haptic assembly. In FIG. 7, an intermediate adjusted position is being retained by ratchet engagements.

Figure 8:
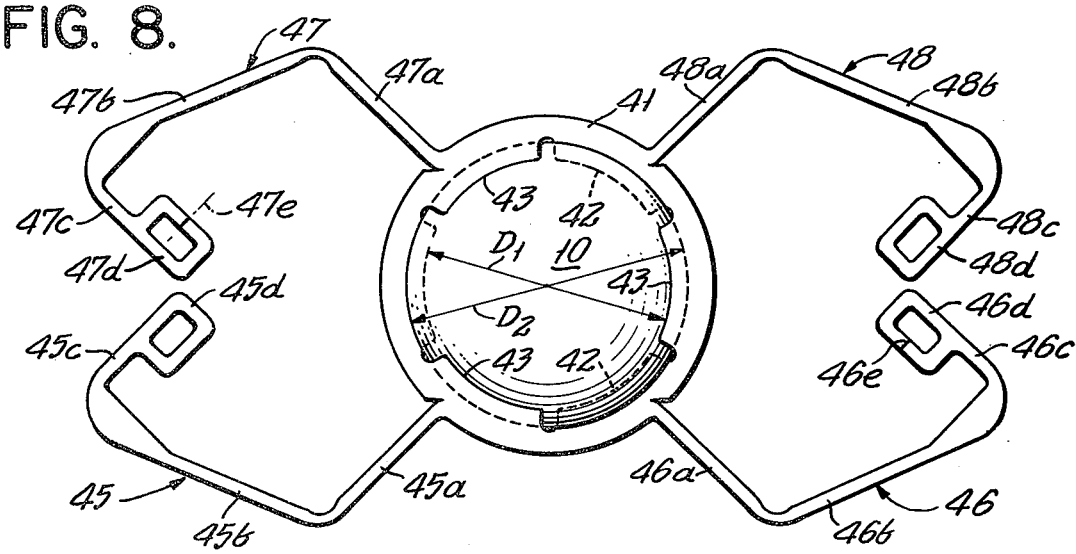
Figure 9:
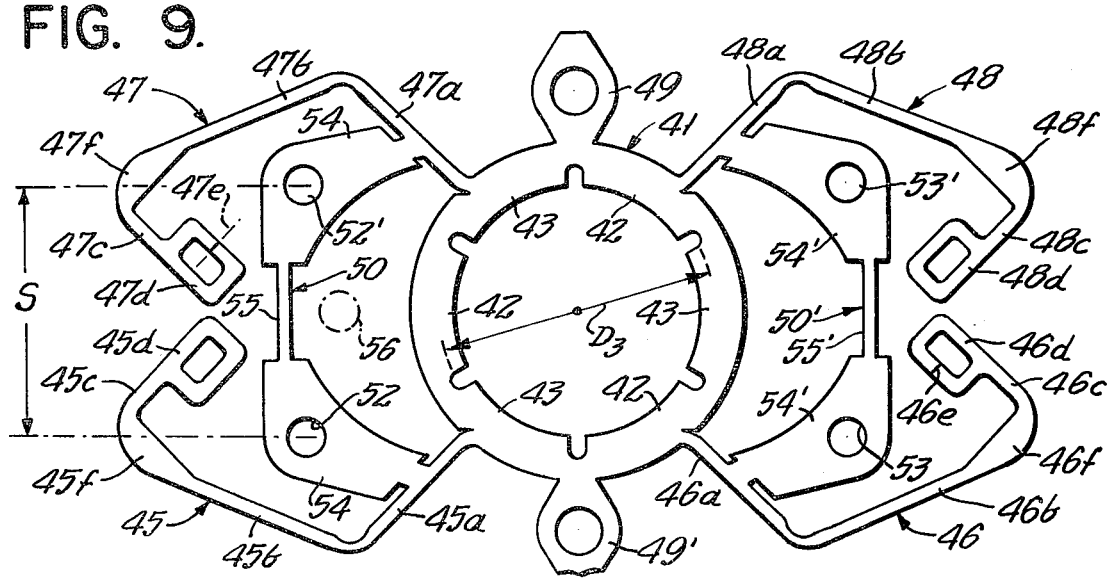
FIG. 9 is a blank outline for haptic structure in FIG. 8.

The embodiment of FIG. 8 represents structure having very much the initial appearance of FIG. 1, but involving only a single-piece haptic 40 which in its initial blank form is as depicted in FIG. 9. The body 41 of haptic 40 is again a circumferentially continuous annulus, with its inner edge slitted at angularly spaced locations and to a depth $D_3$ which slightly exceeds the peripheral diameter of lens element 10. These slits are shown to define six radially inward compliant tabs, one set (42) of three of which is axially deflected for axially loaded engagement with one axial side of the lens element, and the remaining set (43) of which is in angularly interlaced similar retaining engagement with the other axial side of the lens element.

In FIG. 9, all four foot elements 45-46-47-48 of haptic 40 are seen to be integrally formed with body 41 but to be in more outwardly spread relation than for the case of the otherwise similar foot elements 25-26-27-28 of FIGS. 1 to 3. They are characterized by root portions, intermediate portions, generally radially inward end portions and loop formations as described for FIG. 1 and are therefore shown with the same qualifying symbolism. However, to effect the described mutually guided and radially yieldable relation between adjacent foot elements (45-47, 46-48) of each pair, it is necessary to subject all foot elements to compliant deflection, thus assuring that all possible radii of ultimate chamber-wall engagement will be associated with at least some resilient loading in the radially outward direction.

For manipulative purposes in aid of achieving the indicated relationship, the blank of FIG. 9 is shown with integrally formed diametrically opposed apertured locating tabs 49-49' which will be understood to be severed when the foot-assembly operation has been completed. Also, a severable bridge 50 integrally interconnects root portions 45a-47a, and a similar bridge 50' interconnects root portions 46a-48a. Pin-location apertures 52-52' (53-53') characterize spaced relatively massive arms 54(54') of each bridge 50(50'), with narrow and therefore relatively flexible central interconnection 55(55') of the involved arms. The span S between centers of apertures 52-52' (53-53') is so selected that, with the blank of FIG. 9 jig-pin retained via apertures of tabs 49–49', each of the apertures 52–52' may be brought into retained engagement with the same jig pin (suggested at 56), thus compliantly bending root portions 45a–47a toward each other, to the point where loop formation 47d registers with root formation 45a and loop formation 45d registers with root formation 47a. In the process of such bending, (a) the loop formation 47d (and remaining portions of foot 47) is threaded through the loop 45d of foot 45, (b) the narrow interconnection 55 is flexibly doubled, and (c) loop formation 47d, having been previously locally cut as suggested by alignment 47e, may be assembled into retaining relation with root portion 45a. The described process is duplicated to establish the correspondingly engaged relation of foot elements 46–48, whereupon tabs 49–49' and bridge connections to portions (45a ... 48a) may be severed, to produce the haptic configuration of FIG. 8.

It is to be noted that the substantially straight radial nature of root portions 45a ... 48a, at regions of guidance by engaged loop portions 45d ... 48d, enables fillet-stiffened corners 45f ... 48f to serve as relatively inflexible stabilizing feet which are independently displaceable against gently compliant bending action, primarily along the length of the associated angularly extensive intermediate portion 45b ... 48b, and via locally weakened angular connection between portions 45b ... 48b and their associated root portions 45a ... 48a. For a completed lens and haptic assembly having corners 45f ... 48f initially tangent to a circle of 13.5-mm diameter, the range of independent radially inward displaceability of each such corner exceeds 1 mm, so that the assembled article is ultimately self-stabilizing both as to eye-chamber wall departures from circularity and as to eye-chamber diameters less than 13.5 mm, within a collapsible range of 2-mm.

Figure 10:
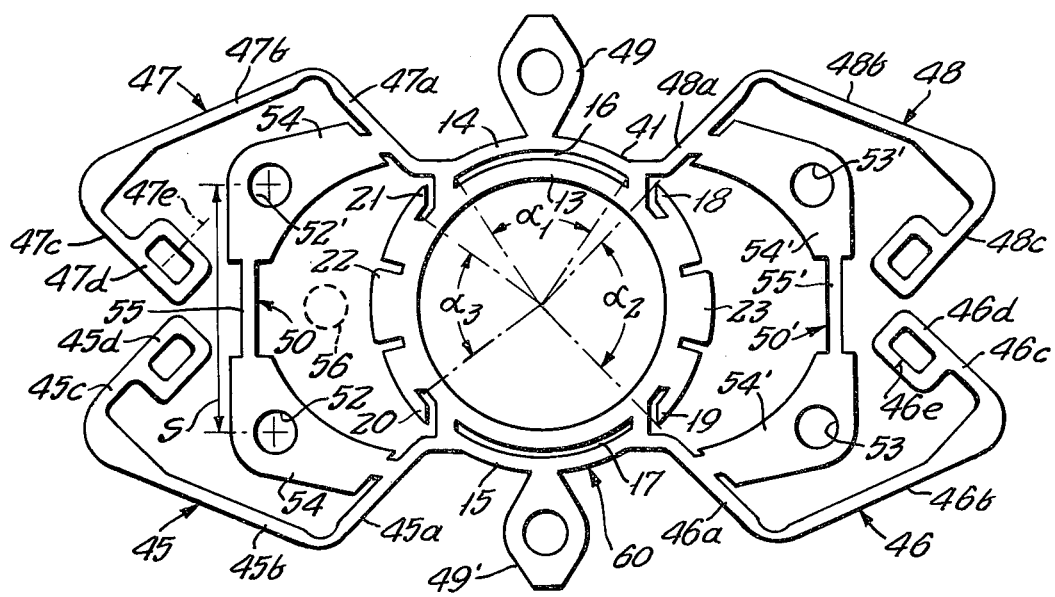
FIG. 10 is a blank outline for a modification of FIG. 9.
Figure 11:
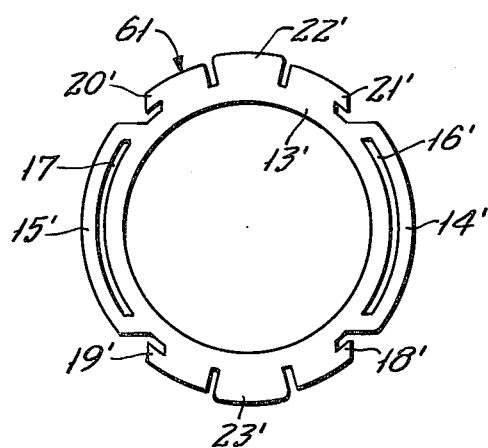
FIG. 11 is a blank outline for additional haptic structure used with the blank of FIG. 10.

The blank of FIG. 10 will be recognized for its outer resemblance to the blank of FIG. 9, but the annular body portion 60 thereof embodies the hook and slot configuration described for the blanks of FIGS. 2 and 5, wherein lens-periphery engagement is circumferentially continuous. The blank of FIG. 10 will establish such lens contact to one axial side of the lens periphery, and similar contact with the opposite axial side is established via a suitably hook-and-slot characterized second body annulus 61, per the blank configuration of FIG. 11. Since hook and slot engagements for FIGS. 10 and 11 correspond to those described for FIGS. 2 and 3, the same symbolism is adopted for such details in FIGS. 10 and 11.

The particular blank of FIG. 10 is shown for the case of legs 45–46 integrally united to the annular body portion 60 at ends of the arcuate tab 15, and with legs 47–58 integrally united at ends of the arcuate tab 14. It will be understood, however, that legs 45–46–47–48 may be integrally connected to body 60 at angular offset from such relation, as for example near the hook formations, but that in any event the annular second haptic part 61 may have hook-and-slot retention to body portion 60 of a thus modified four-leg haptic.

Reference has been made to thin-sheet compliant flexible material for the described haptic structures. This represents my preference, and I indicate my further preference to employ a stable, strong, flexible polyimide, selected for commercial availability and autoclavability. The precise formation of described blank configurations is preferably achieved through photolithographic techniques which are described in one or more of the patent disclosures referred to in the above-mentioned patents. With all forms described herein, the flexible sheet material is suitably 0.002 to 0.008-inch thick.

The described structures will be seen to achieve all stated objects and to provide an improved product suited to particular needs, and especially adaptable to use of identical lithographically fabricated body blanks which are nevertheless readily adaptable to a variety of patient chamber-wall limitations. These structures will also be understood to lend themselves to simple techniques of implantation, as by use of suture or the like filament to draw all foot formations to their most compliantly stressed radially inward condition of minimum outer radius (for example by threading the releasable filament through apertures 35g ... 38g of FIGS. 4, 5 and 6), the filamentary retention being released after insertion into the eye, to then allow all feet to establish their lightly outwardly loaded contact with the eye-chamber wall.

While the invention has been described in detail for the preferred forms shown, it will be understood that modifications may be made without departing from the invention. For example, the adjustably engaged foot elements of the invention have all been described as if their relation were in substantially a single plane, but it will be appreciated that essentially the same foot relations and descriptions apply for the situation in which, for example, a slight axially offsetting uniform permanent bend or crease is formed in the juncture of each root portion to the adjacent region of the involved annular body. In that event, the foot contacts with the chamber wall, for example the anterior chamber, may stabilize at the scleral-ridge region in essentially a single radial plane, in reference to the optical axis of lens element 10, but at axial offset from the annular-body region of lens retention, thus assuring a predetermined axial offset of say 0.5 mm from the iris.

Figure 12:
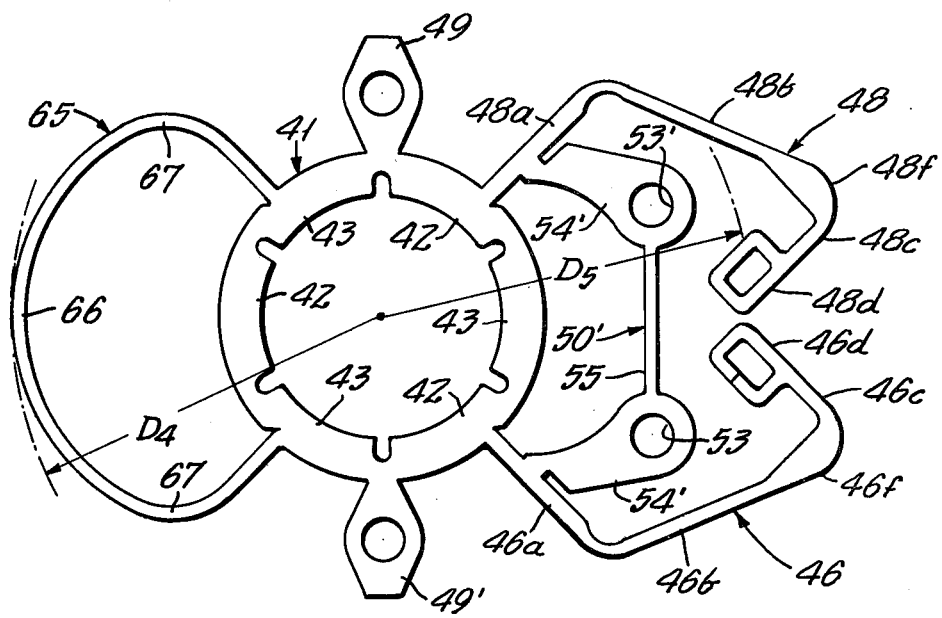
FIGS. 12 and 13 are similar blank outlines to illustrate further modifications.

Also by way of example, as for example, when the surgeon who has planned to install a lens and haptic of the assembled FIG. 8 variety, but who is confronted after initial surgery with the fact that local damage within the eye, in his opinion, precludes installation of a four-point independent haptic suspension, it is convenient to have a lens and haptic of FIG. 12 variety.

The haptic blank of FIG. 12 will be recognized for its close similarity to the central body 41 and one of the two pairs of leg formations (46–48) of the blank of FIG. 9; for this reason, component elements of FIG. 12 corresponding to those of FIG. 9 are shown with the same reference numbers. The point of difference is that in FIG. 12 the other pair (45–47) from the FIG. 9 configuration has been replaced with a single loop or bail formation 65, characterized by an outer gently bowed region 66 for eye-chamber footing engagement, and by sharper bends 67 having integral root connection to body portion 41. The bowed region 66 offers an elongate arc of wall contact, whereby localized stress of a damaged membrane can be minimized, and the independently yieldable other foot regions 46f–48f remain to provide major stabilizing accommodation to more healthy tissue at the diametrically opposite region of the chamber wall. Preferably, the radius of unstressed outer limit of bow 66 should be selected for tangential stabilizing engagement with a chamber-wall circle of diameter $D_4$ equal to or slightly greater than (e.g., 0.5 mm greater than) dictated by dimensions of the eye which is to receive the implant. And for reference purposes, FIG. 12 additionally indicates an arcuate portion of the circle of diameter D₅ to which foot regions 46f and 48f are tangent when assembled (loop 46d to root 48a; and loop 48d to root 46a), preference being indicated for diameter D₅ to equal or slightly exceed diameter D₄, in view of the fact that legs 46–48 are more gently radially inwardly compliant than is the loop formation 66.

Figure 13:
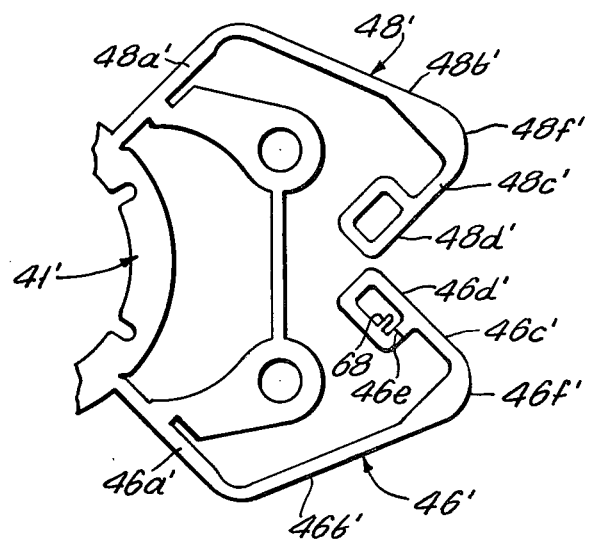

FIG. 13 is a fragmentary diagram of a modified formation of the loop configuration of the haptic leg that is severed to permit assembly to the other leg of a given pair, as in the general style of haptic blanks of FIGS. 9 and 10. As in FIGS. 9 and 10, only one loop (46d') of a given pair (46d'–48d') is severed (at 46e'). The preference is to make this cut (46e') on the short inner portion of loop 46d' and to integrally form an arm 68 extending within the loop to the extent of substantially straddling the cut 46e'. It will be appreciated that this technique enables loop-to-root assembly as before, but in addition the arm 68 provides a safety margin against accidental loss of such assembly, as in the course of surgical manipulation.

Although mention has been made as to applicability of presently disclosed structures in the anterior chamber of an eye, it will be understood that such structures are also applicable for posterior-chamber implantation.

What is claimed is:

1. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, and a plurality of angularly spaced lens-positioning foot elements having cantilevered radially compliant connection to at least one of said body members; a first of said foot elements having a radially outward root portion connected at one end to its body member and having an angularly offsetting intermediate portion integrally connected at one end to the other end of said root portion, and said foot element having a radially inward end portion integrally connected at one end to the other end of said intermediate portion, whereby said radially outward root portion and said radially inward end portion are at angular offset from each other; a second of said foot elements having a radially outward root portion connected at one end to its body member at substantially the location of such angular offset; and interengaging means formed integrally with one of said first and second foot elements and establishing generally radially guided displacement of part of said radially inward end portion of said first foot element along the root portion of said second foot element.

2. The article of claim 1, in which said interengaging means includes a retaining-detent formation establishing detent retention of a radially inward position of said intermediate portion.

3. The article of claim 1, in which said retaining-detent formation is one of a plurality, for establishing a selected one of a plurality of different inward positions of said intermediate portion.

4. The article of claim 1, in which the angular offset between root portions of said first and second foot elements is approximately π/2 radians.

5. The article of claim 1, in which said second foot element has an angularly offsetting intermediate portion integrally connected at one end to the other end of the associated root portion, said second foot element having a radially inward end portion integrally connected at one end to the other end of the associated arcuate intermediate portion, the radially outward root portion of said second foot element and the radially inward end portion of said second foot element being at angular offset from each other to substantially the same but opposite extent of the corresponding offset for said first foot element, and further interengaging means formed integrally with the other of said first and second foot elements and establishing generally radially guided displacement of part of the radially inward end portion of said second foot element along the root portion of said first foot element.

6. The article of claim 1, in which the radially outward root portion and the angularly offsetting intermediate portion of said first foot element merge in a single generally arcuate bow to substantially the location of generally radially guided engagment with said second foot element.

7. The article of claim 6, in which in the region of generally radially guided engagement said second foot element is arcuate and conforms generally to the arcuate bow of said first foot element.

8. The article of claim 1, in which the radially outward root portion and the angularly offsetting intermediate portion of said first foot element are angularly connected substantially straight portions, the location of their angular connection being such as to establish an effective center of intermediate-portion flexure wherein said interengaging means involves a range of generally radially related engagements of said first and second foot elements.

9. The article of claim 1, in which said first foot element is one of two at substantially diametrically opposed location of body member connection, and in which said second foot element is one of two at substantially diametrically opposed locations of body member connection.

10. As an article of manufacture, a mounting-adapter element of compliant sheet material for intraocular chamber-stabilized mounting of a lens element of circular peripheral contour, comprising an annular body member having a central opening defined by an inner-rim formation having a minimum inner diameter less than the outer diameter of the lens element and for axial-retaining abutment with one axial side of the rim of the lens element, means carried at the radially outer region of said body member for axial-retaining abutment with the other axial side of the rim of the lens element, and a plurality of angularly spaced lens-positioning feet formed integrally with the outer edge of said body member and extending radially outward of said body member, the feet of an angularly adjacent pair being each integrally formed with an angularly offsetting portion extending toward the other foot of said pair, first interengagement means formed integrally at the free end of one of the feet of said pair and having slidable engagement along the other foot of said pair, and second interengagement means formed integrally at the free end of said other foot and having slidable engagement along said one foot.

11. The article of claim 10, in which said means comprises a second body member having a circumferentially continuous centrally open inner-rim formation of inner diameter less than the outer diameter of the lens element.

12. The article of claim 10, in which said means comprises plural retaining-lug formations formed integrally with said body at angularly spaced locations.

13. The article of claim 1 or claim 9, in which all said foot elements are integrally formed with a single one of said body members.

14. The article of claim 1, in which said first foot element is integrally formed with one of said body members and said second foot element is integrally formed with the other body member.

15. The article of claim 9, in which two of said foot elements are integrally formed with one of said body members and the remaining two of said foot elements are integrally formed with the other body member.

16. An an article of manufacture, an optically finished intraocular lens element having a generally circular periphery about its optical axis, and a mounting adapter for said lens element; said adapter being of compliant sheet material and comprising an annular body member having a central opening defined by an inner-rim formation having a minimum inner diameter less than the outer diameter of the lens element and in axial-retaining abutment with one axial side of the rim of the lens element, means carried at the radially outer region of said body member in axial-retaining abutment with the other axial side of the rim of the lens element, and a plurality of angularly spaced lens-positioning feet formed integrally with the outer edge of said body member and extending radially outward of said body member, the feet of an angularly adjacent pair being each integrally formed with an angularly offsetting portion extending toward the other foot of said pair, first interengagement means formed integrally at the free end of one of the feet of said pair and having slidable engagement along the other foot of said pair, and second interengagement means formed integrally at the free end of said other foot and having slidable engagement along said one foot.

17. The article of claim 16, in which said means comprises a second annular body member having a central opening defined by an inner-rim formation having a minimum diameter less than the outer diameter of the lens element.

18. The article of claim 16, in which said mounting-adapter element is a single piece of integrally formed sheet material, said means comprising plural angularly spaced radially inward retaining lugs which characterize said inner-rim formation, said lugs being adapted for successively opposite axial directions of compliant deflection for rim retention of said lens element.

19. As an article of manufacture, a mounting-adapter element of compliant sheet material for intraocular chamber-stabilized mounting of a lens element of circular peripheral contour, comprising an annular body member having a central opening defined by an inner-rim formation having a minimum inner diameter less than the outer diameter of the lens element, said inner-rim formation comprising plural retaining-lug formations for alternate axial-retaining abutment with the respective axial sides of the rim of the lens element, and a plurality of angularly spaced lens-positioning feet formed integrally with the outer edge of said body member and extending radially outward of said body member, the feet of an angularly adjacent pair being each integrally formed with an angularly offsetting portion extending toward the other foot of said pair, first interengagement means formed integrally at the free end of one of the feet of said pair and having slidable engagement along the other foot of said pair, and second interengagement means formed integrally at the free end of said other foot and having slidable engagement along said one foot.

20. The article of claim 10 or claim 19, in which said lens-positioning feet iinclude a second pair in diametrically opposed relation to said first-mentioned pair.

21. The article of claim 10 or claim 19, in which said lens-positioning feet include a single loop integrally formed with the outer edge of said body member and extending over an arcuate range which is substantially diametrically opposed to said pair.

22. The article of claim 10 or claim 19, in which the first interengagement means is a first integral loop formation with said other foot slidable in said first loop formation, and in which said second interengagement means is a second integral loop formation with said one foot slidable in said second loop formation.

23. The article of claim 22, in which one of said loops is locally severed to facilitate assembly.

24. The article of claim 23, in which the loop which is severed has an integrally formed arm extending inwardly of said loop and effectively straddling the region in which said loop is severed.

* * * * *